United States Patent
Lang et al.

(10) Patent No.: US 7,151,177 B2
(45) Date of Patent: Dec. 19, 2006

(54) PROCESS FOR THE PREPARATION OF HIGHLY PURE TRIETHYLENE DIAMINE

(75) Inventors: Ortmund Lang, Quirnbach (DE); Bernd Rumpf, Hockenheim (DE); Matthias Frauenkron, Freinsheim (DE); Thomas Manderbach, Ludwigshafen (DE); Bernd Stein, Seeheim-Jugenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 245 days.

(21) Appl. No.: 10/488,978

(22) PCT Filed: Sep. 11, 2002

(86) PCT No.: PCT/EP02/10197

§ 371 (c)(1), (2), (4) Date: Mar. 9, 2004

(87) PCT Pub. No.: WO03/022851

PCT Pub. Date: Mar. 20, 2003

(65) Prior Publication Data

US 2004/0220405 A1      Nov. 4, 2004

(30) Foreign Application Priority Data

Sep. 13, 2001   (DE)   ................................ 101 45 117

(51) Int. Cl.
*C07D 487/00*   (2006.01)
(52) U.S. Cl. ...................................................... 544/352
(58) Field of Classification Search ..................... None
See application file for complete search history.

(56) References Cited

U.S. PATENT DOCUMENTS 3,993,651 A    11/1976   Keating ....................... 260/268
6,627,756 B1    9/2003   Riechers et al. ............ 544/352

FOREIGN PATENT DOCUMENTS

EP    1 070 717    7/2000

OTHER PUBLICATIONS

Derwent 2002-734027/80.
Derwent 2001-193111/20.

*Primary Examiner*—Zachary C. Tucker
(74) *Attorney, Agent, or Firm*—Novak Druce & Quigg, LLP

(57) ABSTRACT

Highly pure triethylenediamine is obtained by a process in which triethylenediamine is freed from high boilers and then the triethylenediamine is vaporized from the mixture thus obtained and is passed into a liquid solvent. The process makes it possible in particular to obtain highly pure solutions of triethylenediamine. Crystallization is generally unnecessary.

20 Claims, No Drawings

PROCESS FOR THE PREPARATION OF HIGHLY PURE TRIETHYLENE DIAMINE

The present invention relates to a process for the preparation of highly pure triethylenediamine (TEDA). In said process, TEDA is vaporized and is passed in vapor form into a liquid solvent and the TEDA is, if required, isolated from the resulting solution, after the high boilers have been separated off before the TEDA is passed into a solvent. The TEDA solution can however be used as such in the conventional applications without further purification.

TEDA is an important catalyst for the preparation of polyurethane foams. TEDA is present as a solid at room temperature. Various processes are known for its preparation and also for its purification including those which are disclosed in the publications mentioned below:

DE-A 24 42 929; U.S. Pat. No. 3,297,701; DE-A 36 34 258; DE-A-17 45 627; DE-A 37 18 395; EP-A 111 928; EP-A-382 055; EP-A 842 935; EP-A 842 936; EP-A 831 096; EP-A 952 152 and U.S. Pat. No. 5,741,906.

The processes known to date for the preparation of TEDA lead to the formation of product mixtures which, in addition to TEDA, also contain water, byproducts, such as piperazine and high molecular weight compounds, and any solvent used in the reaction. TEDA is usually isolated from these mixtures by batchwise or continuous distillation or rectification and is generally purified in a subsequent step by crystallization or recrystallization.

TEDA can be handled without a deterioration in quality, in particular in the color and color stability, in the odor and in the purity, only with comparatively high expense.

In general, a very pure, odorless and pure white TEDA is required for the known, conventional applications. The applications mentioned below disclose processes which are said to give a corresponding TEDA quality:

DE-A 26 11 069; DE-A 28 49 993 and JP-A 49 048 609.

The disadvantage of these processes is that they do not give the TEDA in the desired quality.

The Applicant's patent applications DE 199 33 850.7 of Jul. 23, 1999 and DE 199 62 455.0 of Dec. 22, 1999 relate to a process for the preparation of pure TEDA, in which TEDA is vaporized and the TEDA vapor is passed into a liquid solvent, and the TEDA is crystallized from this solution.

The Applicant's application DE 101 00 943.7 of Jan. 10, 2001 describes a process for the preparation of a solution of pure TEDA, wherein TEDA is vaporized from a mixture containing a solvent or a diluent which has a boiling point of from 175 to 250° C. at atmospheric pressure, and the TEDA vapor is passed into a liquid solvent. Pure TEDA of high quality is obtained by subsequent crystallization of the TEDA from the solution thus obtained.

By means of the processes according to the Applicant's two abovementioned patent applications, it is possible to obtain a TEDA of excellent purity and quality. The last process step, i.e. the crystallization of the TEDA from the solution obtained after the quench, is unavoidable in some cases, for example when TEDA of very high quality and purity is desired. If such a TEDA is to be present in solid form, this crystallization step or at least isolation of the TEDA from the solution is an obligatory process step and presents no further problem. However, TEDA is frequently used in the form of a solution in corresponding applications, in particular when used as a catalyst in polyurethane preparation. For this purpose, the TEDA crystallized beforehand from a solution must be dissolved again. It is evident that it is desirable to have a process for the preparation of highly pure TEDA which gives such a TEDA meeting high requirements without the crystallization step.

It is an object of the present invention to provide a process which makes it possible to obtain highly pure TEDA or highly pure TEDA solutions without a crystallization being required after the TEDA quench.

We have found that this object is achieved by a process for obtaining highly pure TEDA, in which crude TEDA is freed from high boilers and then the TEDA is vaporized and is passed into a liquid solvent.

It has been found that a TEDA of high purity is obtained if the high boilers are separated off before vaporization and passage of the TEDA into a solvent (TEDA quench).

Preferably, the vaporization step effected prior to passing into a solvent is carried out in the form of a distillation, in particular a distillation for the purification of the TEDA. In this distillation, the components which are responsible for a deterioration in the quality of the TEDA are formed only in minor amounts, if at all, if the high boilers are separated off beforehand according to the invention.

In the processes known to date for obtaining pure TEDA by a TEDA quench, the crude TEDA was vaporized, generally distilled. Here, the high boilers formed in the prior synthesis of the TEDA were present in the bottom product of the distillation. The TEDA obtained after the quench still contained impurities which necessitated crystallization of the TEDA from the solution obtained.

By means of the novel process, on the other hand, a solution which contains a TEDA of high purity and which can generally be used directly, for example as a catalyst in polyurethane preparation, is obtained after the quench. Of course, the TEDA can also be isolated as such after crystallization from the solution obtained after the quench. The TEDA obtainable in this manner then has a high purity. Purities of >90%, preferably >95%, in particular >99%, are achieved in this manner.

The high boilers can be separated off by suitable methods known to a person skilled in the art for separating high-boiling and low-boiling components. Preferably, the separation is effected by distilling off the low boilers, including TEDA, from the solution obtained after the TEDA synthesis. The high boilers remain in the bottom product. The high boilers are frequently discarded but can, if desired, also be worked up.

The TEDA is then isolated from the low boiler fraction by distillation. In this distillation, a temperature of <200° C., in particular <180° C., should preferably be maintained. At these temperatures, advantageously small amounts of byproduct are formed. If said temperatures are substantially exceeded, undesirably large amounts of byproduct generally form. The pressure which prevails during this distillation is in general from 0.5 to 1.5 bar. After the separation by distillation, the TEDA vapor, which, according to the invention, has a purity of >90, preferably >95, in particular >99, % by weight, is passed into a liquid solvent. According to the invention, pure TEDA is obtained in this quench. Said TEDA can, as mentioned above, be used in the form of the solution obtained after the quench or, if desired, obtained therefrom by crystallization in a manner known per se.

In one variant of the present invention, the mixture obtained after the high boiler fraction has been separated off is not directly separated and the resulting TEDA subjected to a quench, but the mixture freed from high boilers is first dissolved, according to DE 101 00 943.7, in a solvent or diluent. The TEDA is then distilled off from the solution thus obtained and is quenched. This variant is preferably used when a particularly pure TEDA quality is desired.

In a further variant of the present invention, the low boilers having a lower boiling point than TEDA, for example ammonia, ethylamine or water, are first separated by distillation from the remaining product mixture obtained after synthesis. Preferably, temperatures of from 95 to 120° C. and pressures of from 0.5 to 1.5 bar are maintained therein. The high boilers are then separated from the mixture obtained after said low boilers have been separated off, and the remaining low boilers containing TEDA are worked up according to the invention. The possible process variants, for example the vaporization from a solvent or diluent, can also be used.

Otherwise, the novel process is carried out as described in the Applicant's applications DE 199 33 850.7, 199 62 455.0 and DE 101 00 943.7. Those process steps described in said applications and involving the purification of TEDA which do not comprise separating off the high boilers are an integral part of the process according to the present application and are hereby incorporated by reference. The processes are once again described briefly below.

By passing the TEDA vapor into a liquid solvent (TEDA quench), the formation of undesired byproducts which lead to a deterioration in quality is decisively reduced.

Suitable solvents for this TEDA quench are a multiplicity of organic solvents. Examples include aliphatic, cyclic or acyclic hydrocarbons, in particular cyclic and acyclic, branched or straight-chain alkanes or alkane mixtures, for example n-pentane, isopentane, cyclopentane, hexane, cyclohexane, heptane, octane and petroleum ether, chlorinated aliphatic hydrocarbons, in particular chlorinated alkanes, for example dichloromethane, trichloromethane, dichloroethane and trichloroethane, aromatic hydrocarbons, for example benzene, toluene and xylenes, chlorinated aromatic hydrocarbons, for example chlorobenzene, alcohols, for example methanol, ethanol, ethylene glycol and 1,4-butanediol, and polyether alcohols, in particular polyalkylene glycols, for example diethylene glycol and dipropylene glycol, ketones, in particular aliphatic ketones, for example acetone, methyl ethyl ketone and diethyl ketone, aliphatic carboxylic esters, for example methyl acetate and ethyl acetate, aliphatic nitriles, for example acetonitrile and propionitrile, ethers, for example dioxane, tetrahydrofuran, diethyl ether and ethylene glycol dimethyl ether, and mixtures of the abovementioned solvents.

An aliphatic hydrocarbon or a polyalkylene glycol, in particular a saturated cyclic or acyclic, aliphatic hydrocarbon of 5 to 8 carbon atoms, for example pentane, hexane, cyclohexane or heptane, or dipropylene glycol, is preferably used as a solvent for the TEDA quench. The optional crystallization of the pure TEDA from the TEDA solution prepared according to the invention can be effected by the method known to a person skilled in the art. The TEDA crystals obtained by a subsequent multistage, preferably one-stage, crystallization are highly pure.

The TEDA vapor is passed into the liquid solvent in a quench apparatus, preferably a falling-film condenser (thin-film, trickle-film or downflow condenser) or in a nozzle apparatus. The TEDA vapor can be fed cocurrently with or countercurrently to the liquid solvent. It is advantageous to pass the TEDA vapor into the quench apparatus from above. Tangential feeding of the liquid solvent at the top of the falling-film condenser or feeding of the liquid solvent through one or more nozzles is furthermore advantageous for completely wetting the inner surface of the quench apparatus.

The amount of solvent used is chosen from points of view of expediency. In general, the procedure is such that solutions having a TEDA content of from about 1 to 50, preferably from 20 to 40, % by weight are obtained, depending on the type of solvent.

In general, the temperature in the TEDA quench is established by heating the solvent used and/or the quench apparatus to 20 to 100° C., preferably 30 to 60° C.

The absolute pressure in the TEDA quench is in general from 0.5 to 1.5 bar.

If, in the purification of the TEDA, the latter is vaporized, according to DE 101 00 943.7, from a mixture with a solvent or diluent, the solvent or diluent preferably has a boiling point of from 180 to 250° C., more preferably from 180 to 230° C., in particular from 190 to 210° C., at atmospheric pressure.

Particularly suitable solvents or diluents which contain the mixture from which the TEDA is vaporized are inert polar aprotic solvents, for example alkyl-2-pyrrolidones, for example N-methyl-2-pyrrolidone (NMP), 1-ethyl-2-pyrrolidone, 1,5-dimethyl-2-pyrrolidone and 1-isopropyl-2-pyrrolidone, ethers, for example diethylene glycol diethyl ether, triethylene glycol dimethyl ether and triethylene glycol diethyl ether, ketones, for example acetophenone and propiophenone, lactones, for example γ-butyrolactone, sulfoxides, for example dimethyl sulfoxide, carboxylic esters, for example dimethyl fumarate, nitriles, for example benzonitrile, and ureas, for example 1,3-dimethylimidazolidin-2-one (DMEU) and tetramethylurea, cyclic or acyclic hydrocarbons, in particular saturated cyclic or acyclic hydrocarbons, for example undecane, dodecane, cis-decalin and trans-decalin, chlorinated aliphatic hydrocarbons, for example 1-chlorooctane and 1,1-dichlorooctane, aromatic hydrocarbons, nitroaromatics and phenols, for example naphthalene, n-butylbenzene, phenol, cresol, nitrobenzene and nitrophenol, chlorinated aromatic hydrocarbons, for example 1,2-dichlorobenzene, benzyl chloride, 1,2,3,4-tetramethylbenzene and 1,2,3,5-tetramethylbenzene, alcohols, for example benzyl alcohol, 2-ethylhexanol, 1-octanol, isodecanol, 1,2-propanediol, 1,3-propanediol, ethylene glycol, diethylene glycol, 1,2-propylene glycol, 1,3-propylene glycol, 1,2-butanediol, 1,3-butanediol, 2,3-butanediol, 1,4-butanediol, neopentylglycol, diethylene glycol monomethyl ether and dipropylene glycol, primary, secondary and tertiary amines, for example tri-n-butylamine, benzylamine, aniline, N-ethylaniline, N,N-dimethylaniline and N,N-diethylaniline, N-alkylamides, for example N-methylformamide and N-methylacetamide and mixtures thereof.

Polar aprotic solvents or diluents having an $E^N_T$ value of from 0.1 to 0.6, in particular from 0.2 to 0.5, especially from 0.3 to 0.45, are particularly preferred.

(For a definition of the $E^N_T$ value, cf. Ch. Reichardt, Solvents and solvent effects in organic chemistry, 2nd Edition, VCH 1988.)

Very particularly preferred solvents are NMP and ethylene glycol.

The solvent or diluent which contains the mixture from which the TEDA is vaporized is preferably added to the still impure TEDA after the high boilers have been separated off.

The solvent or diluent can be used in a single pass or, after the high boilers have been separated off, as a circulated solution.

The amount of solvent or diluent used is chosen from points of view of expediency. In general, the procedure is such that solutions or mixtures having a TEDA content of from about 1 to 90, preferably from 40 to 70, % by weight are obtained, depending on the type of solvent or diluent.

The vaporization of the TEDA, optionally from a mixture of this with a solvent or diluent, can be effected according to the methods and conditions familiar to a person skilled in the art, for example in a distillation or rectification apparatus, if required the TEDA being initially taken together with the solvent or diluent.

The TEDA vapor is preferably obtained at the top or in a side take-off of a distillation column. In the novel process, the TEDA vapor generally has a purity greater than 90, preferably greater than 95, in particular greater than 99, % by weight.

The time between production of the TEDA vapor used in the novel process and TEDA quench is advantageously $\leq 10$ seconds. The TEDA to be purified can be obtained by known processes, for example by reacting monoethanolamine, diethanolamine, triethanolamine, ethylenediamine, diethylenetriamine, triethylenetetramine, piperazine, N-(2-hydroxyethyl)piperazine, N,N'-bis(2-hydroxyethyl)piperazine, N-(2-aminoethyl)-piperazine, N,N'-bis(2-aminoethyl)piperazine, morpholine or mixtures thereof over a catalyst, for example metal pyrophosphates or metal phosphates, for example an alkaline earth metal monohydrogen phosphate, zeolites, zirconium phosphate, $Al_2O_3$, $SiO_2$, phosphorus-containing $TiO_2$ or $ZrO_2$, at elevated temperatures, in general from 250 to 450° C. Usually, the pressure is from 0.1 to 50, in particular from 0.1 to 5, bar here. Optionally, the reaction can be carried out in the presence of an inert polar aprotic solvent, such as N-alkylpyrrolidones, for example N-methylpyrrolidone, dioxane, tetrahydrofuran, dialkylformamides, for example dimethylformamide, dialkylacetamides, for example dimethylacetamide, and of an inert carrier gas, for example $N_2$ or Ar.

Optionally, the TEDA can be crystallized and can be isolated by solid-liquid separation.

According to a preferred embodiment, the novel process can be carried out as follows:

A mixture which contains TEDA and can be obtained, for example, as the reaction discharge in a continuous process by reacting ethylenediamine and piperazine in a gas-phase reactor at from 320 to 420° C. and from 0.5 to 1.5 bar in the presence of a solvent, for example water, of a carrier gas, for example $N_2$ or Ar, and of a zeolite catalyst, for example according to patent application DE 100 61 863.4, is passed into a distillation apparatus comprising a distillation column having, for example, about 15 theoretical plates. Here, low boilers, for example ammonia, ethylamine or water, are separated off at a top temperature of from 95 to 120° C. and a pressure of from 500 mbar to 1.5 bar via the top. The bottom discharge is pumped into a further distillation column having about 30 theoretical plates. At a pressure of from 500 mbar to 1.5 bar, the high boilers are eliminated via the bottom discharge in this column. At a top temperature of from 150 to 170° C., TEDA and piperazine are pumped into a further distillation column having about 30 theoretical plates. At a pressure of 500 mbar to 1.5 bar, piperazine is separated off via the top take-off in this column and optionally recycled to the synthesis reactor.

The bottom discharge, which contains traces of undesired decomposition products, is partly discarded and/or recycled to the preceding column.

In a side take-off of the column, TEDA having a purity of >95, in particular >99, % by weight is taken off in vapor form via a partial condenser and is cooled directly and abruptly and simultaneously dissolved in a solvent, for example dipropylene glycol, 1,4-butanediol or monoethylene glycol, at from 30 to 100° C., preferably from 30 to 60° C., in a falling-film condenser (TEDA quench).

EXAMPLES

Example 1 (Comparative Example, not according to the Invention)

The experiments were carried out in a 4 l (catalyst volume) stainless steel salt bath reactor heated by means of electrical heating tapes. The catalyst used was a zeolite in the form of extrudates (diameter about 2 mm, length about 30 mm) (catalyst bed).

The feedstock of 1 000 g/h and 3 l(S.T.P.)/h (l(S.T.P.)= volume in liters converted to standard temperature and pressure conditions) of nitrogen were passed at atmospheric pressure into the salt bath reactor heated to 350° C. (catalyst space velocity: 0.3 kg of feedstock per l of catalyst (bed volume) per hour).

The feedstock had the following composition (data in % by weight):

| | |
|---|---|
| Ethylenediamine | 30% |
| Piperazine | 20% |
| Water | 50% |

The reaction product in vapor form was condensed at 80° C. in a quench with circulated liquid which consisted of previously obtained liquid reaction product (see below).

The analysis of the condensate gave the following composition (data in % by weight):

| | |
|---|---|
| Ammonia | 3% |
| Piperazine | 17% |
| Triethylenediamine | 23% |
| Water | 54% |
| Remainder | High boilers and other byproducts |

The uncondensed fractions were discharged into a distillation column (K200) after a gas-liquid separator.

A part of the liquid reaction product was cooled and was used as liquid circulation (for the reaction discharge quench). Another part was pumped continuously by means of a pump into a further distillation column K200. The glass column having a diameter of 50 mm was equipped with 30 bubble trays. The reflux ratio was about 1:1.

The low boilers (ammonia, ethylamine, water) were taken off in liquid form at the top of the column at atmospheric pressure and a top temperature of 96° C.

The bottom discharge of the distillation column was pumped continuously at 155° C. into a downstream distillation column (K300).

The glass column K300 having a diameter of 50 mm was equipped with 60 bubble trays. The reflux ratio was about 10:1. Piperazine was taken off in liquid form at the top of the column at atmospheric pressure and a top temperature of 150° C. and was recycled to the reactor.

The bottom discharge of the distillation column K300 was pumped continuously at 184° C. into a further distillation column (K400).

The analysis of the bottom discharge gave the following composition (data in % by weight):

| | |
|---|---|
| Piperazine | 0.2% |
| Triethylenediamine (TEDA) | 83% |
| Remainder | High boilers and other byproducts |

The glass column K400 having a diameter of 50 mm was equipped with 50 bubble trays. The reflux ratio was about 8:1.

The high boilers were discharged continuously at 230° C. via the bottom of the column, and the forward flow temperature of the oil-heated evaporator was 260° C. TEDA was taken off in vapor form at the top of the column and was cooled abruptly at about 30° C. in the solvent dipropylene glycol and simultaneously dissolved (TEDA quench). A falling-film condenser (trickle-film or downflow condenser) in which TEDA vapor was passed in from above was used for the TEDA quench. The dipropylene glycol was fed in tangentially at the top of the falling-film condenser. The resulting solution had the following composition (data in % by weight):

| | |
|---|---|
| Piperazine | 0.7% |
| Ethylpiperazine | 0.08% |
| Triethylenediamine (TEDA) | 30.0% |
| Dipropylene glycol | 68.5% |
| Remainder | Byproducts |

The TEDA thus obtained had inadequate properties with respect to its color and its odor and was therefore not marketable.

This TEDA/DPG solution had an APHA color number of 80.

The TEDA obtained had an odor of cyclic saturated 5-ring N-heterocycles or other cyclic 6-ring N-heterocycles and/or aromatic 5- or 6-ring N-heterocycles.

The required high temperature in the stripping part of the last distillation column (product temperature up to 230° C.) led to considerable thermal stresses for the TEDA and for the high boiler and hence the formation of undesired decomposition products. By balancing the feed and discharge streams of the column, it is possible to determine a piperazine source in the bottom of column K400. The decomposition of high boilers (e.g. aminoethylpiperazine, 1,2-dipiperazinoethane) was assumed to be the PIP source in the bottom of K400.

Example 2 (According to the Invention)

The experiment was carried out as described in example 1, except that the high boilers were first separated off from the bottom discharge of distillation column K200 in the downstream distillation column K300.

The glass column K300 having a diameter of 50 mm was equipped with 60 bubble trays. The reflux ratio was about 6:1. The high boilers were discharged continuously at 220° C. via the bottom of the column, and the forward flow temperature of the oil-heated evaporator was 240° C.

The analysis of the bottom discharge gave the following composition (data in % by weight):

| | |
|---|---|
| Piperazine | 63% |
| Triethylenediamine | 36% |
| Remainder | Byproducts |

The glass column K400 having a diameter of 50 mm was equipped with 60 bubble trays. The reflux ratio was about 8:1. Piperazine was discharged continuously at 148° C. at the top of the column and was recycled to the reactor. TEDA was taken off in vapor form from the side take-off and cooled abruptly at about 30° C. in the solvent dipropylene glycol and simultaneously dissolved (=TEDA quench). A falling-film condenser (trickle-film or downflow condenser) in which TEDA vapor was passed in from above was used for the TEDA quench. Dipropylene glycol was sprayed in at the top of the falling-film condenser. The resulting solution had the following composition (data in % by weight):

| | |
|---|---|
| Piperazine | 0.01% |
| Ethylpiperazine | 0.01% |
| Triethylenediamine (TEDA) | 34.0% |
| Dipropylene glycol | 65.9% |
| Remainder | Byproducts |

This TEDA/DPG solution had an APHA color number of 32 and can be used directly as a catalyst in the preparation of polyurethanes.

The TEDA obtained had no odor of cyclic saturated 6-ring N-heterocycles and/or aromatic 5- or 6-ring N-heterocycles. Further working-up by subsequent crystallization is not necessary but may be carried out if desired, a highly pure TEDA being obtained.

We claim:

1. A process for obtaining triethylenediamine having a purity of at least 90% by weight, wherein crude triethylenediamine is freed from high boilers and then the triethylenediamine is vaporized from the mixture thus obtained and is passed into a liquid solvent.

2. A process as claimed in claim 1, wherein the vaporization of the triethylenediamine is carried out in the form of a distillation.

3. A process as claimed in claim 2, wherein the distillation is a distillation for purification of the TEDA from low boilers.

4. A process as claimed in claim 1, wherein the separation of the high boilers from low boilers contained in the crude triethylenediamine is effected by distilling off the low boilers, including triethylenediamine, from the solution obtained after the triethylenediamine synthesis, the high boilers remaining in the bottom product.

5. A process as claimed in claim 1, wherein before the high boilers are separated off, low boilers contained in the crude triethylenediamine and having a boiling point lower than that of triethylenediamine are separated by distillation from the remaining product mixture obtained after synthesis.

6. A process as claimed in claim 1, wherein the triethylenediamine is distilled off at <200° C. and from 0.5 to 1.5 bar after the high boilers have been separated off.

7. A process as claimed in claim 6, wherein the triethylenediamine is distilled off at <180° C.

8. A process as claimed in claim 1, wherein the mixture obtained after the high boiler fraction has been separated off is first dissolved in a solvent or diluent and the triethylenediamine is then distilled off from the solution thus obtained and is passed into a liquid solvent.

9. A process as claimed in claim 1, wherein a solvent from the group consisting of aliphatic, cyclic and acyclic hydrocarbons, chlorinated aliphatic hydrocarbons, aromatic hydrocarbons, chlorinated aromatic hydrocarbons, alcohols, ketones, aliphatic carboxylic esters, aliphatic nitriles, ethers, and mixtures of the abovementioned solvents are used as solvents into which the vaporized triethylenediamine is passed.

10. A process as claimed in claim 9, wherein the solvent is chosen from cyclic and acyclic, branched and straight-chain alkanes and alkane mixtures, chlorinated alkanes, benzene, toluene, xylenes, chlorobenzene, methanol, ethanol, ethylene glycol, 1,4-butanediol, polyether alcohols, polyalkylene glycols, acetone, methyl ethyl ketone, diethyl ketone, methyl acetate, ethyl acetate, acetonitrile, propionitrile, dioxane, tetrahydrofuran, diethyl ether and ethylene glycol dimethyl ether.

11. A process as claimed in claim 1, wherein the triethylenediamine vapor is passed into the liquid solvent in a quench apparatus or in a nozzle apparatus, the triethylenediamine vapor being fed concurrently with or countercurrently to the liquid solvent.

12. A process as claimed in claim 11, wherein the quench apparatus is a falling-film condenser.

13. A process as claimed in claim 1, wherein the solvent or diluent which contains the mixture from which the triethylenediamine is vaporized is selected from the group consisting of ethers, ketones, lactones, Sulfoxides, carboxylic esters, nitriles, ureas, cyclic and acyclic hydrocarbons, chlorinated aliphatic hydrocarbons, aromatic hydrocarbons, nitroaromatics, phenols, chlorinated aromatic hydrocarbons, alcohols, primary, secondary and tertiary amines, N-alkylamides and mixtures thereof.

14. A process as claimed in claim 13, wherein the solvent is a polar aprotic solvents or diluents having an ENT value of from 0.1 to 0.6.

15. A process as claimed in claim 14, wherein the solvent has an $E^N_T$ value from 0.2 to 0.5.

16. A process as claimed in claim 14, wherein the solvent has an $E^N_T$ value from 0.3 to 0.45.

17. A process as claimed in claim 1, wherein the steps of
  i) freeing the crude triethylenediamine from high boilers and
  ii) vaporizing the triethylenediamine from the mixture thus obtained are carried out by employing a separate distillation column for each step.

18. A process as claimed in claim 5, wherein the low boilers are selected from the group consisting of ammonia, ethylamine and water.

19. A process as claimed in claim 11, wherein said triethylenediamine vapor is passed into the quench apparatus from above.

20. A process as claimed in claim 1, wherein the solvent or diluent which contains the mixture from which the triethylenediamine is vaporized is a polar aprotic solvent.

* * * * *